(12) United States Patent
Hoshino

(10) Patent No.: US 9,805,161 B2
(45) Date of Patent: Oct. 31, 2017

(54) MEDICAL CARE DATA DISPLAY CONTROL DEVICE, METHOD AND PROGRAM

(71) Applicant: FUJIFILM Corporation, Tokyo (JP)

(72) Inventor: Takashi Hoshino, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 485 days.

(21) Appl. No.: 14/472,015

(22) Filed: Aug. 28, 2014

(65) Prior Publication Data

US 2015/0066530 A1    Mar. 5, 2015

(30) Foreign Application Priority Data

Sep. 2, 2013 (JP) .................................. 2013-180928

(51) Int. Cl.
| | |
|---|---|
| G06Q 50/22 | (2012.01) |
| G06Q 50/24 | (2012.01) |
| G06F 19/00 | (2011.01) |

(52) U.S. Cl.
CPC ........ *G06F 19/322* (2013.01); *G06F 19/3487* (2013.01)

(58) Field of Classification Search
CPC ............ G06F 17/3055; G06F 19/3487; G06F 17/30958; G06F 3/04847; G06F 19/322; G06Q 30/0643; G06Q 10/04; G06Q 50/24; G06Q 50/22; H04L 43/06; H04L 41/0813

See application file for complete search history.

(56) References Cited

U.S. PATENT DOCUMENTS

| | | |
|---|---|---|
| 5,447,164 A | 9/1995 | Shaya et al. |
| 7,297,129 B2 | 11/2007 | Kinouchi et al. |
| 2007/0088525 A1 | 4/2007 | Fotiades et al. |
| 2007/0198301 A1 | 8/2007 | Ayers et al. |
| 2014/0068490 A1 | 3/2014 | Ayers et al. |

(Continued)

FOREIGN PATENT DOCUMENTS

| | | |
|---|---|---|
| JP | H 02-11129 A | 1/1990 |
| JP | 2001-118008 A | 4/2001 |
| JP | 2004-078310 A | 3/2004 |

(Continued)

OTHER PUBLICATIONS

Extended European Search Report dated Jan. 4, 2016.

(Continued)

*Primary Examiner* — Maroun Kanaan
(74) *Attorney, Agent, or Firm* — McGinn IP Law Group, PLLC

(57) ABSTRACT

A medical care data display control device for displaying medical care data of a plurality of items obtained in chronological order is disclosed. The device includes: a hidden time period determining length setting unit in which a hidden time period determining length used to determine whether or not to hide a part of a displayed time period of the medical care data is set; a determination unit that determines whether or not there is a time period which contains no medical care data and is equal to or longer than the hidden time period determining length; and a display control unit that hides, if it is determined by the determination on unit that there is a time period which contains no medical care data and is equal to or longer than the hidden time period determining length, all or a part of the time period which contains no medical care data.

14 Claims, 9 Drawing Sheets

(56) References Cited

U.S. PATENT DOCUMENTS

2014/0257861 A1    9/2014    Ayers et al.

FOREIGN PATENT DOCUMENTS

| JP | 2004-248793 A | 9/2004 |
| JP | 2011-123652 A | 6/2011 |
| JP | 2012-079200 A | 4/2012 |
| WO | WO 2008/086092 A1 | 7/2008 |

OTHER PUBLICATIONS

Extended European Search Report (English Language version) dated Nov. 18, 2014.
"Axis Tutorial", Oct. 15, 2011, XP055150736, Retrieved from the Internet: URL: http://web.archive.org/web/20111015031014/http://www.dotnetcharting.com/documentation/Currnet/axis_tutorial.pdf [retrieved on Nov 4, 2014].
Stephen Few: "Line Graphs and Irregular Intervals: An Incompatible Partnership", Dec. 21, 2008, pp. 1-11, XP055150727, Retrieved from the Internet: URL: http://web.archive.org/web/20081221080240/http://wvvw.perceptualedge.com/articles/visual_business_intelligence/line_graphs_and_irregular_intervals.pdf [retrieved on Nov. 4, 2014].
Japanese Office Action dated Sep. 1, 2015 with an English translation thereof.
European Office Action dated Jan. 4, 2016.

| | 4/28 | 4/29 | 4/30 | 5/1 | 5/2 | 5/3 | 5/4 | 5/5 | 5/6 | 5/7 | 5/8 | 5/9 | 5/10 | 5/11 |
|---|---|---|---|---|---|---|---|---|---|---|---|---|---|---|
| | 1 | 1 | 1 | 1 | 1 | 1 | | | | | 2 | 2 | 2 | 2 |
| | 4 | 4 | | | | | | | | | | 2 | 2 | 2 |
| TEST A | | 0.4 | | | | 0.2 | | | 0.2 | | | | 0.5 | |
| TEST B | | 1.8 | | | | 3.7 | | | 3.5 | | | | 2.4 | |
| TEST C | | 0.45 | | | | 0.9 | | | 0.24 | | | | 0.49 | |
| TEST D | | 0.3 | | | | 0 | | | 0.3 | | | | 1 | |
| TEST E | | 7.1 | | | | 7.1 | | | | | | | 7.7 | |

FIG.8

| MEDICAL CARE ITEM | 1/5 FRI. | 1/6 SAT. | 1/7 SUN. | 1/8 MON. | 1/9 TUE. | 1/10 WED. | 1/11 THU. | 1/12 FRI. | 1/13 SAT. | 1/14 SUN. | 1/15 MON. | 1/16 TUE. | 1/17 WED. |
|---|---|---|---|---|---|---|---|---|---|---|---|---|---|
| BODY TEMPERATURE | 37.5 | 37.4 | 37.4 | 37.5 | 37.5 | 37.6 | 37.9 | 37.6 | 37.6 | 37.5 | 37.4 | 37.4 | 37.5 |
| BLOOD PRESSURE (SYSTOLIC) | 130 | 131 | 131 | 129 | 131 | 132 | 133 | 131 | 130 | 130 | 131 | 130 | 129 |
| BLOOD PRESSURE (DIASTOLIC) | 88 | 85 | 87 | 87 | 86 | 88 | 89 | 87 | 87 | 88 | 88 | 87 | 86 |
| TEST A | | | | 31 | | | | | | | 28 | | |
| TEST B | | | | 125 | | | | | | | 130 | | |
| TEST C | | | | 76 | | | | | | | 81 | | |

FIG.9

| MEDICAL CARE ITEM | 1/8 MON. | 1/15 MON. | 1/22 MON. | 1/29 MON. | 2/5 MON. | 2/12 MON. | 2/19 MON. | 2/26 MON. | 3/5 MON. | 3/12 MON. | 3/19 MON. | 3/26 MON. | 4/2 MON. |
|---|---|---|---|---|---|---|---|---|---|---|---|---|---|
| BODY TEMPERATURE | 37.5 | 37.4 | 37.4 | 37.6 | 37.7 | 37.6 | 37.7 | 37.5 | 37.2 | 37.0 | 37.0 | 36.9 | 36.7 |
| BLOOD PRESSURE (SYSTOLIC) | 129 | 131 | 131 | 132 | 131 | 131 | 132 | 130 | 131 | 129 | 128 | 125 | 123 |
| BLOOD PRESSURE (DIASTOLIC) | 87 | 88 | 86 | 88 | 86 | 87 | 89 | 88 | 87 | 85 | 86 | 85 | 83 |
| TEST A | 31 | 28 | 28 | 30 | 31 | 29 | 29 | 27 | 25 | 23 | 21 | 19 | 19 |
| TEST B | 125 | 130 | 133 | 133 | 135 | 137 | 138 | 137 | 132 | 125 | 119 | 108 | 106 |
| TEST C | 76 | 81 | 82 | 84 | 86 | 86 | 87 | 85 | 82 | 77 | 72 | 65 | 65 |

MEDICAL CARE DATA DISPLAY CONTROL DEVICE, METHOD AND PROGRAM

CROSS-REFERENCE TO RELATED APPLICATIONS

The present application claims priority under 35 U.S.C. §119 to Japanese Patent Application No. 2013-180928, filed on Sep. 2, 2013. The above application is hereby expressly incorporated by reference, in its entirety, into the present application.

BACKGROUND OF THE INVENTION

Field of the Invention

The present invention relates to a medical care data display control device, a medical care data display control method and a medical care data display control program for displaying medical care data of a plurality of items obtained in chronological order.

Description of the Related Art

In recent years, during medical care of a patient by a doctor, medical care data of results of a plurality of tests performed on the patient are displayed on a display device to be used as reference information for diagnosing the name of the disease and determining a treatment plan, etc.

Tests performed on a patient includes various types of tests. When a specific disease of a patient is suspected in actual medical setting, medical care data of each of tests that are considered important for diagnosis of the specific disease is referenced to perform diagnosis or treatment.

However, there may be a case where the number of test items performed on a patient is large. In such a case, the number of displayed items when the medical care data are referenced may be excessively large and it may take a long time to display the medical care data of all the items or it may be difficult to reference the data.

In particular, with respect to nursing care information, such as body temperature and blood pressure, of a hospitalized patient, the number of times of each test is large and therefore the number of data points of the medical care data is very large, resulting in a displayed screen overcrowded with the nursing care information, which makes it difficult to observe medical care data of items other than the nursing care information.

In order to address this problem, a method involving receiving a selection of test items to be displayed and displaying only medical care data of the selected test items is proposed in Japanese Unexamined Patent Publication Nos. 2004-248793, 2(1990)-011129 and 2004-078310, for example.

SUMMARY OF THE INVENTION

However, for example, if test items other than the nursing care information, such as body temperature and blood pressure, are selected and only the medical care data of the selected test items are displayed in order to facilitate viewing the displayed screen, as described above, the medical care data of the nursing care information, which is not selected to be displayed, cannot be observed at a time, and such a display is not appropriate for a case where the nursing care information is also necessary for diagnosis.

One may consider selecting both the items of the nursing care information and other items. In this case, however, if test frequencies of the other items are significantly lower than test frequencies of the items of the nursing care information, the number of displayable data points of the medical care data of the items other than the nursing care information is not sufficient because of limitation on the time period of medical care data displayable on the screen.

Further, the number of data points or the time period of medical care data of test items of interest which the user wishes to observe varies depending on the types of disease and test items, and judgment of the user, such as a doctor, and it is desired to efficiently display medical care data of test items of interest in a flexible manner to meet various situations. For example, there are situations where the user wishes to observe data points of medical care data of test items of interest as many as possible, or the user wishes to also observe medical care data with high test frequency, such as the nursing care information, for some continuous time period.

In view of the above-described circumstances, the present invention is directed to providing a medical care data display control device, a medical care data display control method and a medical care data display control program that allow displaying a sufficient number of data points of medical care data of test items with relatively high test frequency, such as body temperature and blood pressure, and of other test items with low test frequency, and allow flexibly setting the number of data points and a displayed time period of medical care data of test items of interest.

An aspect of the medical care data display control device of the invention is a medical care data display control device for displaying medical care data of a plurality of items obtained in chronological order, the device comprising: a hidden time period determining length setting unit in which a hidden time period determining length used to determine whether or not to hide a part of a displayed time period of the medical care data is set; a determination unit that determines whether or not there is a time period which contains no medical care data and is equal to or longer than the hidden time period determining length; and a display control unit that hides, if it is determined by the determination unit that there is a time period which contains no medical care data and is equal to or longer than the hidden time period determining length, all or a part of the time period which contains no medical care data.

In the medical care data display control device of the invention, the hidden time period may be a time period including at least the hidden time period determining length.

The medical care data display control device may further comprise an item specification receiving unit that receives a specification of an item for which the determination based on the hidden time period determining length is performed among the plurality of items, wherein the determination unit may determine whether or not there is a time period which contains no medical care data of the specified item and is equal to or longer than the hidden time period determining length, and the display control unit may hide, if it is determined that there is a time period which contains no medical care data of the specified item and is equal to or longer than the hidden time period determining length, all or a part of the time period which contains no medical care data of the specified item.

The medical care data display control device may further comprise a hidden time period determining length specification receiving unit that receives a specification of the hidden time period determining length.

The hidden time period determining length may be set in advance.

If it is determined that there is a time period which contains no medical care data and is equal to or longer than the hidden time period determining length, and if there is a time period which contains no medical care data before or after the hidden time period determining length, the display control unit may also hide the time period before or after the hidden time period determining length.

The display control unit may display a marker that allows recognition of the hidden time period.

The display control unit may display the medical care data in the form of a graph.

The display control unit may display the graph with lines connecting the medical care data immediately before the hidden time period and the medical care data in the hidden time period or lines connecting the medical care data immediately after the hidden time period and the medical care data in the hidden time period.

The display control unit may display the medical care data in the form of numerical texts.

When the time period which contains no medical care data is hidden, the display control unit may additionally display the medical care data for a time period that is different from the displayed time period before the time period which contains no medical care data is hidden.

An aspect of the medical care data display control method of the invention is a medical care data display control method for displaying medical care data of a plurality of items obtained in chronological order, the method comprising: determining whether or not there is a time period which contains no medical care data and is equal to or longer than a hidden time period determining length, the hidden time period determining length being set to be used to determine whether or not to hide a part of a displayed time period of the medical care data; and if it is determined that there is a time period which contains no medical care data and is equal to or longer than the hidden time period determining length, all or a part of the time period which contains no medical care data is hidden.

An aspect of the medical care data display control program of the invention is a non-transitory computer readable medium containing a medical care data display control program for causing a computer to function as a medical care data display control device for displaying medical care data of a plurality of items obtained in chronological order, the program causing the computer to function as: a hidden time period determining length setting unit in which a hidden time period determining length used to determine whether or not to hide a part of a displayed time period of the medical care data is set; a determination unit that determines whether or not there is a time period which contains no medical care data and is equal to or longer than the hidden time period determining length; and a display control unit that hides, if it is determined by the determination unit that there is a time period which contains no medical care data and is equal to or longer than the hidden time period determining length, all or a part of the time period which contains no medical care data.

According to the medical care data display control device, method and program of the invention, the hidden time period determining length used to determine whether or not to hide a part of a displayed time period of the medical care data is set, determination as to whether or not there is a time period which contains no medical care data and is equal to or longer than the hidden time period determining length is made, and, if it is determined that there is a time period which contains no medical care data and is equal to or longer than the hidden time period determining length, all or a part of the time period which contains no medical care data is hidden. By hiding a time period which contains no medical care data of a test item with low test frequency, for example, more data points of the medical care data of the test item with low test frequency can be displayed on a screen.

At this time, medical care data of a test item with high test frequency for the time period other than the hidden time period can also be displayed, that is, medical care data of a test item with high test frequency and medical care data of a test item with low test frequency can be displayed at a time, thereby allowing efficient diagnosis based on the medical care data of these test items.

Further, since the user can set the hidden time period determining length depending on the type of disease, the type of test item of interest, or the like, the user can arbitrarily set a time period to be hidden. This allows flexibly setting the number of medical care data of test items of interest and a displayed time period, thereby allowing efficient observation of the medical care data.

BRIEF DESCRIPTION OF THE DRAWINGS

FIG. 2 shows one example of a medical care information display screen in a graph display mode, FIG. 7 shows one example of the medical care information display screen in a numerical display mode, FIG. 8 shows an example of a numerical display of medical care data including body temperature, blood pressure (systolic), blood pressure (diastolic), and tests A to C, and FIG. 9 shows an example where some parts of the time period of the numerical display shown in FIG. 8 are hidden.

DESCRIPTION OF THE PREFERRED EMBODIMENTS

Figure 1:
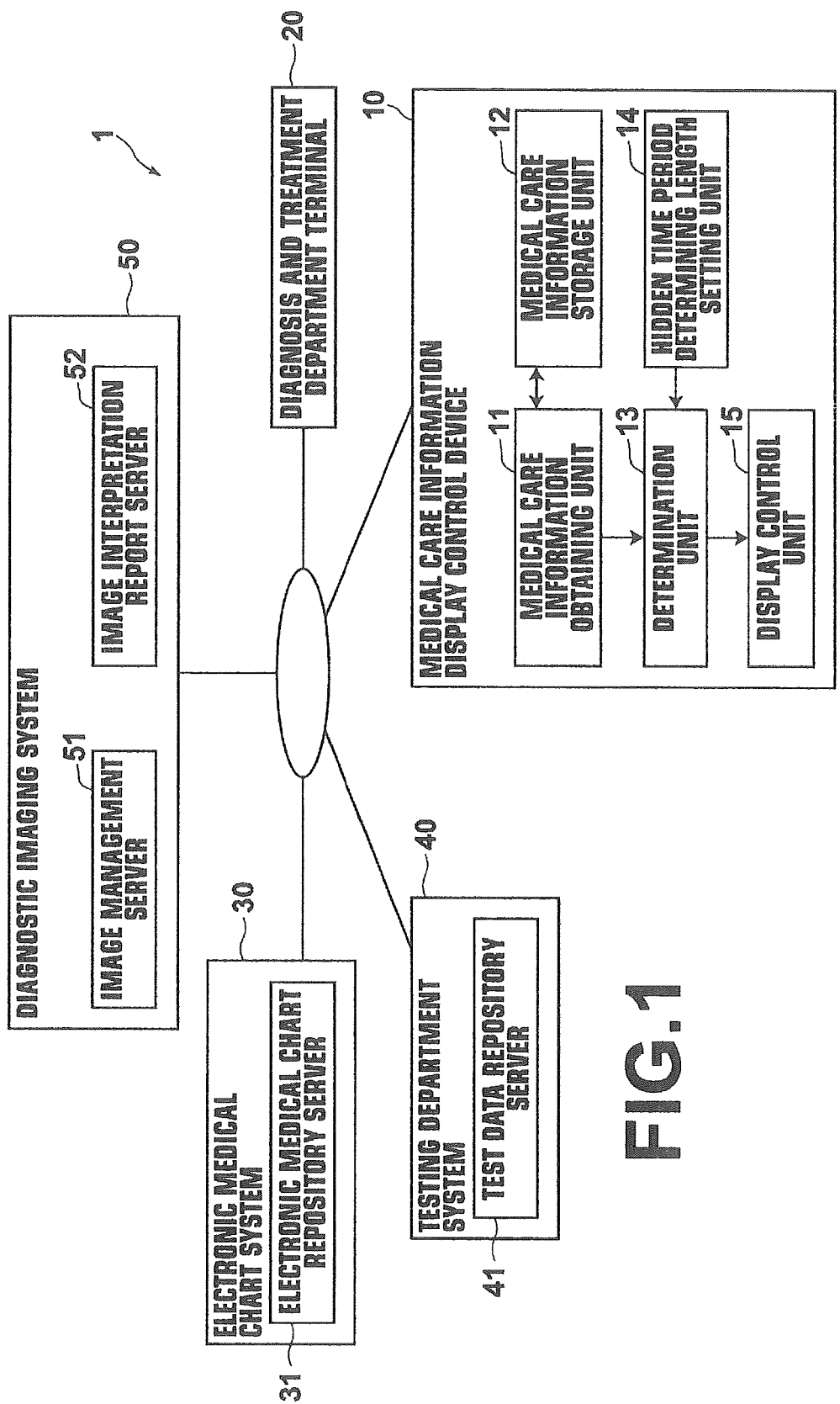
FIG. 1 is a block diagram illustrating the schematic configuration of a medical care information display system employing one embodiment of a medical care data display control device of the invention.

Hereinafter, a medical care information display system employing one embodiment of a medical care data display control device, a medical care data display control method and a medical care data display control program of the present invention will be described in detail with reference to the drawings. FIG. 1 is a block diagram illustrating the schematic configuration of a medical care information display system 1 of this embodiment.

As shown in FIG. 1, the medical care information display system 1 of this embodiment includes a medical care information display control device 10, a diagnosis and treatment department terminal 20, an electronic medical chart system 30, a testing department system 40, and a diagnostic imaging system 50.

The medical care information display control device 10, the diagnosis and treatment department terminal 20, and the systems 30 to 50 of the medical care information display system 1 are connected via a network, such as a wired or wireless LAN or the Internet connection.

First, the medical care information display control device 10 is described. In this embodiment, the medical care information display control device 10 corresponds to the medical care data display control device of the invention.

The medical care information display control device 10 receives identification information of a patient, which is inputted on the diagnosis and treatment department terminal 20, collects medical care information relating to the patient from each of the electronic medical chart system 30, the testing department system 40 and the diagnostic imaging system 50, generates a medical care information display screen by integrating the collected information, and displays the medical care information display screen on the diagnosis and treatment department terminal 20.

Specifically, as shown in FIG. 1, the medical care information display control device 10 includes a medical care information obtaining unit 11, a medical care information storage unit 12, a determination unit 13, a hidden time period determining length setting unit 14, and a display control unit 15.

The medical care information display control device 10 is implemented by installing, on a computer, a medical care information display control program that includes one embodiment of the medical care data display control program of the invention. When the medical care information display control program is executed by the central processing unit (CPU), the medical care information obtaining unit 11, the determination unit 13, the hidden time period determining length setting unit 14, and the display control unit 15 function. The medical care information display control program may be recorded on a recording medium, such as a CD-ROM, or may be downloaded from a server, or the like, via the Internet.

Based on the identification information of the patient inputted on the diagnosis and treatment department terminal 20, the medical care information obtaining unit 11 obtains medical care information linked to the identification information of the patient from servers of the above-mentioned systems via the network. As the medical care information, basic information, such as the name, age and sex of the patient, various medical care data, such as dose of an administered or infused drug, specimen test data and vital data, and medical image information, such as a radiographic image, an ultrasound image, etc. It should be noted that the medical care data may be any data as long as the data are represented by numerical values or texts (character strings) other than numerical values relating to medical care of a patient. In the following description, medical care data represented by numerical values are mainly described. However, the medical care data are not limited to those represented by numerical values, as mentioned above, and may be represented by texts other than numerical values. In a case where the medical care data are represented by texts other than numerical values, the medical care data are displayed in the form of a table, for example, in a numerical display mode, which will be described later. Examples of the medical care data represented by texts other than numerical values may include medical care data indicating whether a test is "performed" or "not performed", and medical care data indicating whether a result of a test is "good" or "poor".

The medical care information obtaining unit 11 once stores, in the medical care information storage unit 12, the medical care information collected from the servers based on the identification information of the patient. The medical care information storage unit 12 is formed by a storage device, such as a hard disk.

In the hidden time period determining length setting unit 14, a hidden time period determining length, which is used when the medical care data are displayed in chronological order on the monitor of the diagnosis and treatment department terminal 20, is set. The hidden time period determining length refers to a time period length that is used to determine whether or not to hide a part of a displayed time period of the medical care data. If there is a time period which contains no medical care data and is equal to or longer than the hidden time period determining length, all or a part of the time period which contains no medical care data is hidden.

This embodiment is configured such that various hidden time period determining lengths can be set by the user, such as a doctor. The hidden time period determining length is changed depending on the medical care items which the user wishes to observe, the number of medical care data which the user wishes to observe at a time, the type of disease, etc. By allowing the user to set various hidden time period determining lengths, the user can display desired pieces of medical care data at a time on the monitor.

As the hidden time period determining length, a given time period, such as one month or one week, for example, is set. Specific examples thereof will be described in detail later. It should be noted that the hidden time period determining length may not necessarily be able to be set by the user, and may be kept as an initial value set in advance in the hidden time period determining length setting unit 14.

The determination unit 13 determines whether or not there is a time period which contains no medical care data and is equal to or longer than the hidden time period determining length. In this embodiment, the user specifies a medical care item of interest (an item for which the determination based on the hidden time period determining length is performed) via the input device of the diagnosis and treatment department terminal 20. Then, the determination unit 13 determines, for the specified medical care item, whether or not there is a time period which contains no medical care data and is equal to or longer than the hidden time period determining length.

The display control unit 15 generates a medical care information display screen based on the medical care information containing the medical care data outputted from the medical care information obtaining unit 11, and outputs the medical care information display screen to the diagnosis and treatment department terminal 20, on which the medical care information display screen is displayed.

Figure 2:
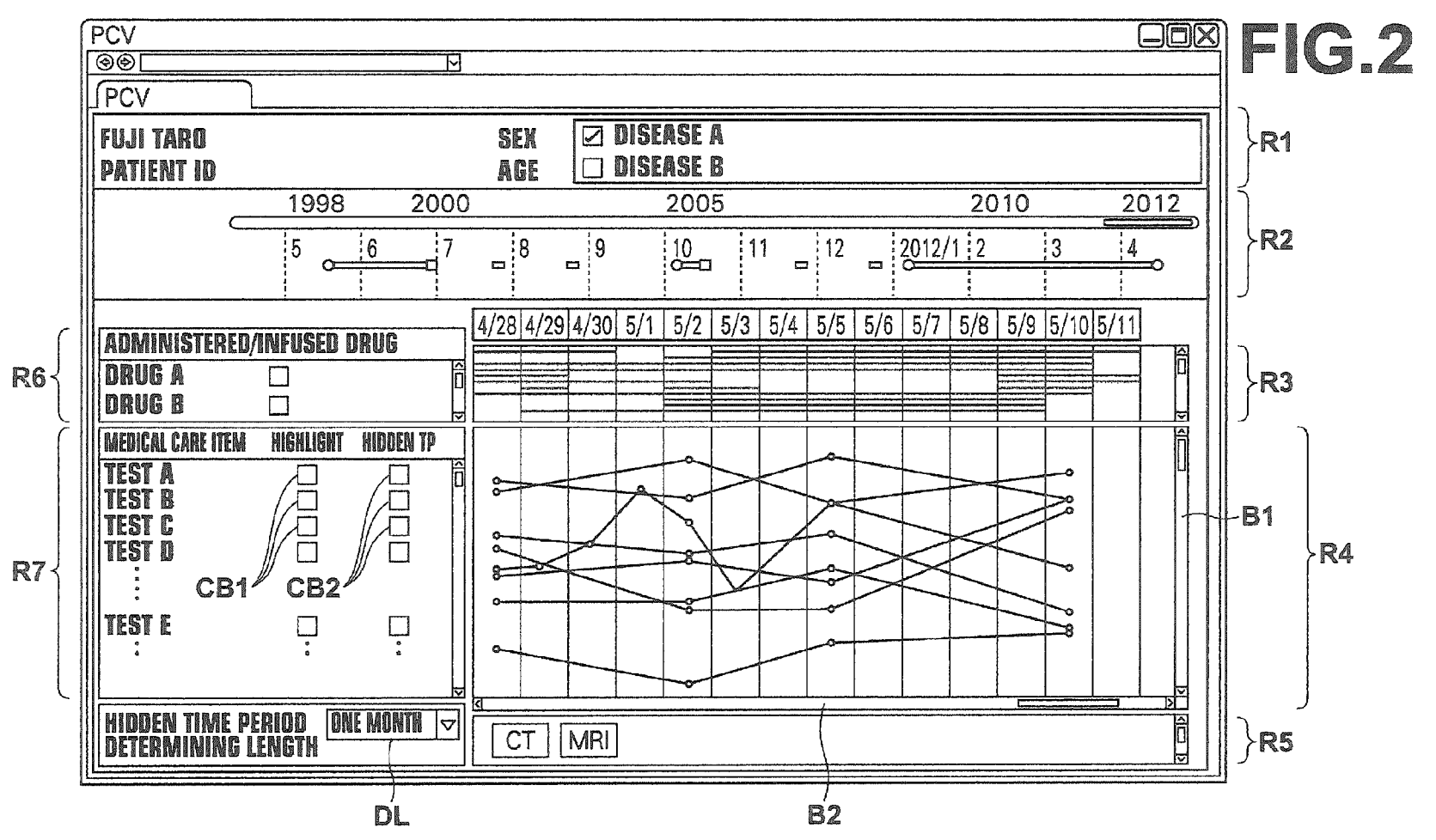

The display control unit 15 can switch the display mode between a graph display mode for displaying the medical care data in the form of a graph and a numerical display mode for displaying the medical care data in the form of numerical texts (character strings). First, the medical care information display screen in the graph display mode is described. FIG. 2 shows one example of the medical care information display screen in the graph display mode.

As shown in FIG. 2, the medical care information display screen includes a basic information display column R1, a medical care period display column R2, a drug administration period display column R3, a medical care data display column R4, a medical image information column R5, an administered drug list display column R6, and a medical care item list display column R7.

In the basic information display column R1, identification information (patient ID) the patient, and the basic information of the patient, such as name, age, sex, history of present illness and past history, etc., are displayed. With respect to the history of present illness and past history, a check box is displayed for each disease, as shown in FIG. 2. A disease with the check box being checked is specified as a disease of interest, and the medical care data and the medical image information relating to the disease are displayed.

In the medical care period display column R2, medical care period, etc., of the patient are displayed, where a time period of each medical care, such as test or treatment, performed on the patient is displayed in the form of a bar chart. In the drug administration period display column R3, a time period of administration or infusion of each drug on the patient is displayed, where a time period of administration or infusion of each drug on the patient is displayed in the form of a bar chart.

In the medical care data display column R4, medical care data of a plurality of medical care items obtained in chronological order are displayed in the form of a line graph. The horizontal axis of the medical care data display column R4 is the time axis, and the vertical axis represents numerical values of the medical care data. The medical care data display column R4 is provided with a scroll bar B1 used to change the range of numerical values for displaying the medical care data, and a scroll bar B2 used to change the displayed time period of the medical care data.

In the medical image information column R5, medical image information of the patient is displayed. Specifically, thumbnail images of images obtained by imaging the patient with a CT (Computed Tomography) apparatus, a MRI (magnetic resonance imaging) apparatus, an ultrasound imaging device, etc., are displayed. When each thumbnail image is clicked on, for example, to be selected, the original image corresponding to the thumbnail image is displayed separately from the thumbnail image, and an image interpretation report on the original image is also displayed.

In the administered drug list display column R6, the type of each drug administered or infused during each drug administration period displayed in the drug administration period display column R3 is displayed in the form of a list. In the administered drug list display column R6, the list of drugs is displayed, and a check box is displayed for each drug. Then, the drug administration period of a drug with the check box being checked is highlighted in the drug administration period display column R3. Specifically, the drug administration period of a drug with the check box being checked is displayed in color, and the drug administration period of a drug that is not checked is displayed in pale gray so as not to draw attention, for example.

In the medical care item list display column R7, medical care items of the medical care data displayed in the medical care data display column R4 are displayed in the form of a list. In the medical care item list display column R7, the list of medical care items is displayed, and two types of check boxes, a highlighting check box CB1 and a hidden time period-determination check box CB2 (which corresponds to the item specification receiving unit), are displayed for each medical care item.

When the highlighting check box CB1 is checked, medical care data of the checked medical care item is highlighted in the medical care data display column R4. Specifically, medical care data of a medical care item with the highlighting check box CB1 being checked is displayed in color, and medical care data of a medical care item that is not checked is displayed in pale gray so as not to draw attention, for example.

The hidden time period-determination check box CB2 receives a specification of a medical care item for which the above-described determination based on the hidden time period determining length is performed. When the hidden time period-determination check box CB2 is checked, the checked medical care item is specified as a medical care item for which the determination based on the hidden time period determining length is performed. Then, the determination unit 13 determines whether or not there is a time period which contains no medical care data of the specified medical care item and is equal to or longer than the hidden time period determining length.

Further, on the medical care information display screen, a drop-down list DL (which corresponds to the hidden time period determining length specification receiving unit) used to set the above-described hidden time period determining length is displayed. The user sets the hidden time period determining length by selecting a desired hidden time period determining length from various time periods shown in the drop-down list DL.

When the graph of the medical care data is displayed in the medical care data display column R4, if there is a medical care item with the hidden time period-determination check box CB2 being checked, and if there is a time period which contains no medical care data of the checked medical care item and is equal to or longer than the hidden time period determining length based on a result of the determination by the determination unit 13, the display control unit 15 hides all or a part of the time period which contains no medical care data.

It should be noted that the number of the medical care item for which the determination based on the hidden time period determining length is performed is not limited to one, and a plurality of medical care items may be specified. In this case, if there is a time period which contains no medical care data of the plurality of specified medical care items and is equal to or longer than the hidden time period determining length, all or a part of the time period which contains no medical care data is hidden. Further, in a case where all the medical care items are specified as medical care items for which the determination based on the hidden time period determining length is performed, if there is a time period which contains no medical care data of all the medical care items and is equal to or longer than the hidden time period determining length, all or a part of the time period which contains no medical care data is hidden. Specific examples thereof will be described in detail later.

The diagnosis and treatment department terminal 20 includes a monitor, and an input device, such as a keyboard and a mouse. On the monitor of the diagnosis and treatment department terminal 20, the medical care information display screen shown in FIG. 2 is displayed. The keyboard and the mouse of the diagnosis and treatment department terminal 20 are used to receive an input of identification information of a patient, an input of the above-described hidden time period determining length, an input of a specification via each of the above-described check boxes, etc.

The electronic medical chart system 30 manages electronic medical charts of a plurality of patients. The electronic medical chart system 30 includes an electronic medical chart repository server 31. In the electronic medical chart repository server 31, an electronic medical chart of each patient is stored with being linked to the identification information of the patient. The electronic medical chart system 30 obtains identification information of a patient inputted on the diagnosis and treatment department terminal 20, and outputs information of the electronic medical chart linked to the identification information to the medical care information display control device 10. The electronic medical chart contains the basic information of the patient, and information of the type and dose of an administered or infused drug, the drug administration period, the history of present illness and the past history, etc.

The testing department system 40 manages specimen test data and test data, such as vital data, of a plurality of patients. The testing department system 40 includes a test data repository server 41. In the test data repository server 41, test data of a plurality of items of each patient are stored with being linked to the identification information of the patient. The testing department system 40 obtains identification information of a patient inputted on the diagnosis and treatment department terminal 20, and outputs the test data linked to the identification information to the medical care information display control device 10. It should be noted that, in one aspect, test data may once have been outputted to be contained in an electronic medical chart and stored in the form of the electronic medical chart. In this case, the test data is outputted from the electronic medical chart to the medical care information display control device 10.

The diagnostic imaging system 50 manages medical image information of a plurality of patients. The diagnostic imaging system includes an image management server 51, and an image interpretation report server 52. In the image management server 51, a radiographic image, etc., of each patient are stored with being linked to the identification information of the patient. The image interpretation report server 52 stores image interpretation reports which are generated by a doctor or doctors while observing radiographic images, etc., and each image interpretation report is stored with being linked to the corresponding radiographic image, or the like, stored in the image management server 51. The diagnostic imaging system 50 obtains identification information of a patient inputted on the diagnosis and treatment department terminal 20, and outputs the radiographic image (s), or the like, and the corresponding image interpretation report (s) linked to the identification information to the medical care information display control device 10.

Figure 3:
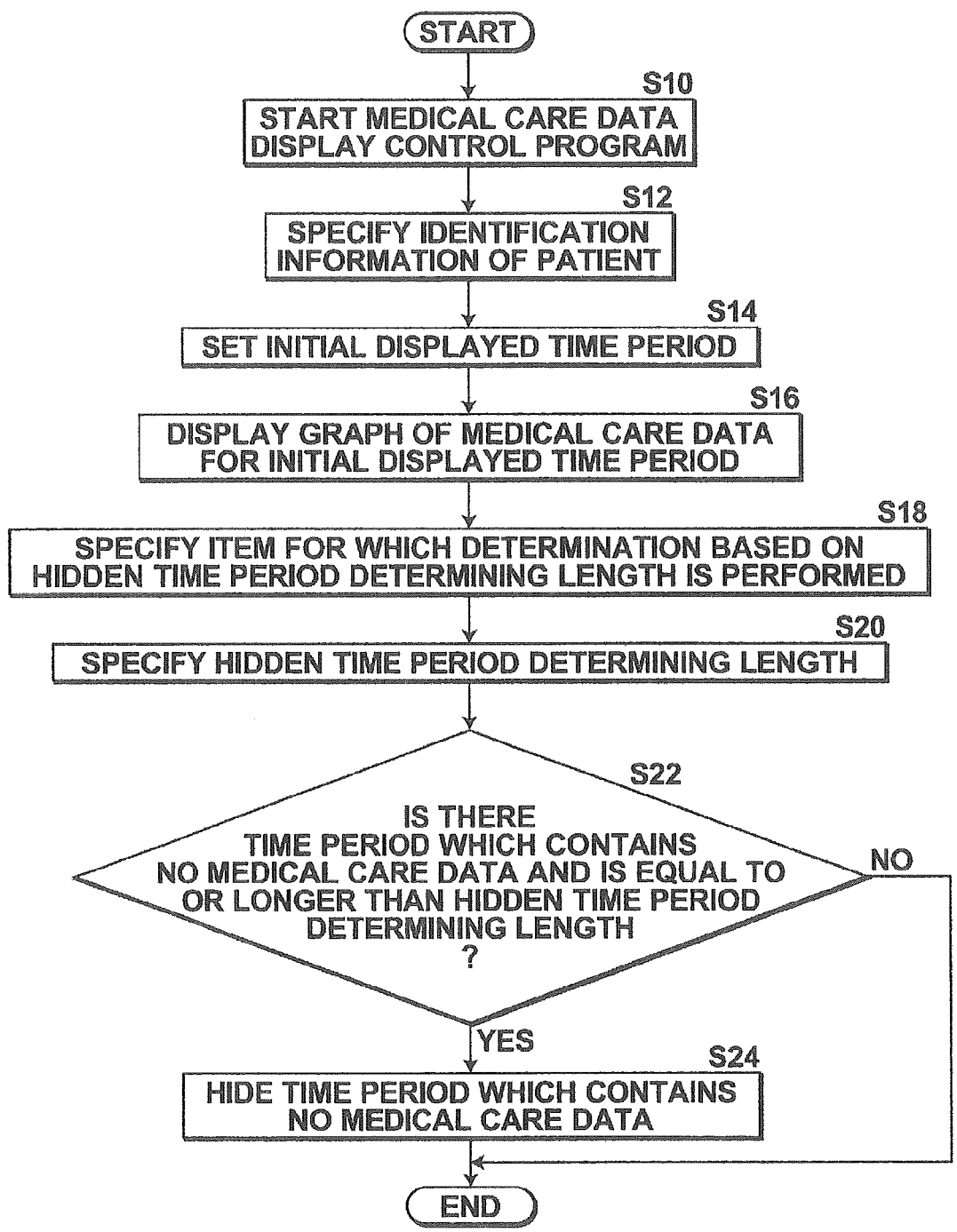
FIG. 3 is a flow chart for explaining operation of the medical care information display system shown in FIG. 1.

Next, operation of the medical care information display system 1 of this embodiment is described with reference to the flow chart shown in FIG. 3. It should be noted that the medical care information display system 1 of this embodiment is characterized by how the medical care data in the above-described medical care data display column R4 is displayed, and therefore this point is mainly described in the following description.

First, the medical care data display control program installed on the medical care information display control device 10 is started in response to an instruction by the user inputted on the diagnosis and treatment department terminal 20 (S10).

Then, identification information of a patient is inputted on the diagnosis and treatment department terminal 20, and the identification information of the patient is obtained by the medical care information obtaining unit 11 of the medical care information display control device 10 (S12).

Based on the inputted identification information of the patient, the medical care information obtaining unit 11 reads out and obtains medical care data of the patient from the test data repository server 41 of the testing department system 40, the electronic medical chart repository server 31 of the electronic medical chart system 30, etc., and once stores the obtained medical care data in the medical care information storage unit 12.

Subsequently, an initial displayed time period of the medical care data to be displayed is set and inputted on the diagnosis and treatment department terminal 20, and information of the initial displayed time period is inputted to the display control unit 15 (S14). The display control unit 15 obtains the medical care data corresponding to the inputted initial displayed time period and displays a graph of the medical care data in the medical care data display column R4 (S16).

Figure 4:
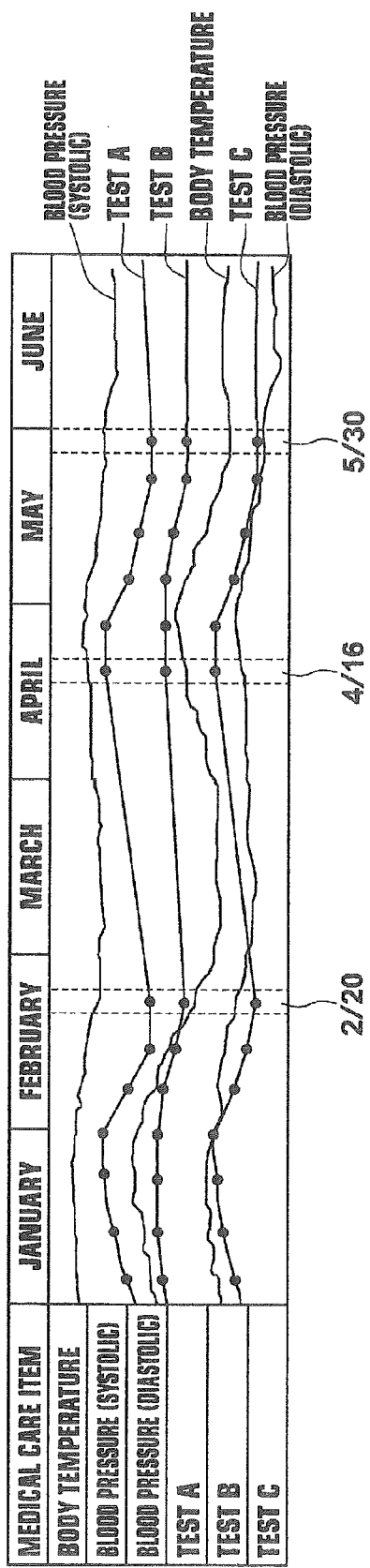
FIG. 4 shows an example of a graph display of medical care data including body temperature, blood pressure (systolic), blood pressure (diastolic), and tests A to C.

Now, specific display examples are described. FIG. 4 shows an example of a graph display based on medical care data of body temperature, blood pressure (systolic), blood pressure (diastolic), and tests A to C for an initial displayed time period, which is set to be from January 1st to June 30th, obtained by the display control unit 15. The horizontal axis of the graph shown in FIG. 4 represents the date and the vertical axis represents the numerical value of each medical care data. It should be noted that, while the body temperature, the blood pressure (systolic) and the blood pressure (diastolic) are medical care data obtained every day, dots corresponding to data points of these items are omitted in the graph shown in FIG. 4 to facilitate visual understanding. The medical care data of the tests A to C are obtained at given time intervals, and dots corresponding to values of the obtained medical care data are shown in the graph shown in FIG. 4. That is, each of the medical care data of the tests A to C is obtained on the date indicated by the corresponding dot.

Then, if the user wishes to observe medical care data of the test A, for example, for a time period longer than the initial displayed time period at a time in an efficient manner in the graph display as shown in FIG. 4, the user checks the hidden time period-determination check box CB2 corresponding to the test A in the medical care item list display column R7 (S18), and selects one of hidden time period determining lengths shown in the drop-down list DL (S20). It is assumed here that a hidden time period determining length of one month is selected and set by the user.

The information specifying the test A and the information of the hidden time period determining length are outputted to the determination unit 13, and the determination unit 13 determines whether or not there is a time period which contains no medical care data of the test A and is equal to or longer than one month (S22).

Figure 5:
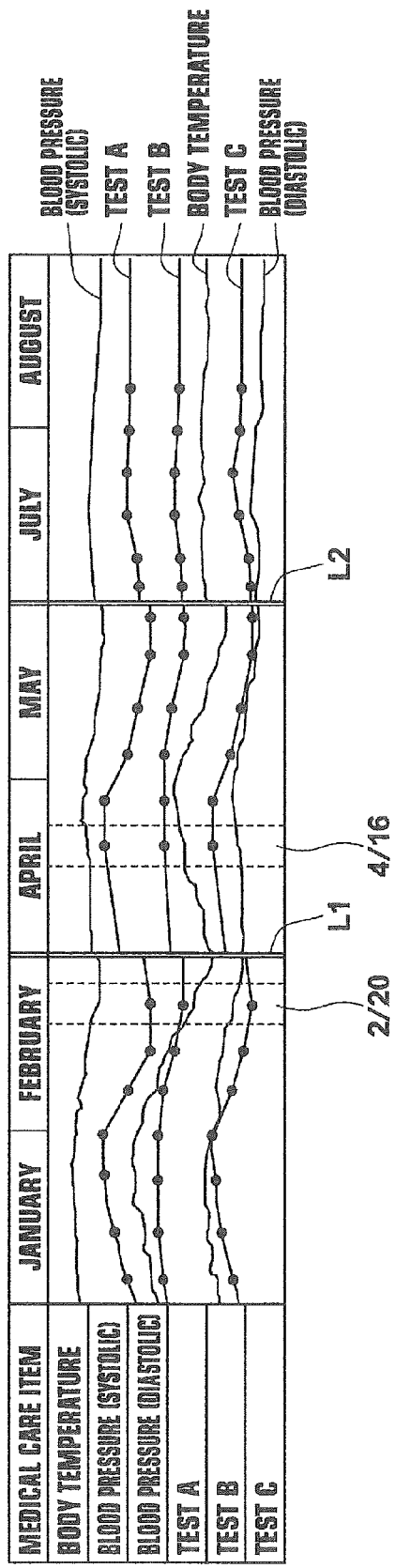
FIG. 5 shows an example where some parts of the time period of the graph shown in FIG. 4 are hidden.

Then, if there is a time period which contains no medical care data of the test A and is equal to or longer than one month, the result of determination is outputted to the display control unit 15, and the display control unit 15 hides the medial care data for the time period which contains no medical care data of the test A (S24). Specifically, in the graph display shown in FIG. 4, for example, a time period of one month which contains no medical care data of the test A is found in March and June. Therefore the result of determination is outputted to the display control unit 15, and the display control unit 15 hides March and June, as shown in FIG. 5. As the result of hiding March and June, a blank is created along the horizontal axis direction of the medical care data display column R4. Then, the display control unit 15 obtains medical care data of all the items for July and August, which is a different time period from the initial displayed time period, and displays a graph of the medical care data with the displayed time period changed to include January to February, April to May, and July to August. That is, when a given time period is hidden, the display control unit 15 obtains additional medical care data for a time period of the same length as the hidden time period and displays the additional medical care data in the graph.

Further, when a given time period is hidden, as described above, it is desirable to display a marker that allows the user to recognize that there is a hidden time period. For example, in the case where March and June are hidden, as in the graph shown in FIG. 5, it is desirable that a boundary line L1 between February and April and a boundary line L2 between May and July be displayed in a different color from other axes, etc., so that they are recognizable by the user. Alternatively, markers, such as arrows or characters, indicating the positions of the boundary line L1 and the boundary line L2 may be displayed.

It should be noted that, when the determination unit 13 determines whether or not there is a time period which contains no medical care data of the test A and is equal to or longer than one month, the starting day of the one month may be set in advance. In the above-described example, the starting day of one month is the first day of each month. However, this is not intended to limit the invention, and the starting day of one month may be the first day of a time period which contains no medical care data of the specified medical care item, for example. For example, in the case where the medical care data of the test A is found until February 20th and no medical care data of the test A is found since February 21st, as shown in FIG. 4, February 21st may be the starting day of one month. Similarly, in the case where the medical care data of the test A is found until May 30th and no medical care data of the test A is found since June 1st, June 1st may be the starting day of one month.

Also, the starting day of a time period hidden by the display control unit 15 may not necessarily be the first day of each month. For example, in the case where no medical care data of the test A is found since February 21st, as in the graph shown in FIG. 4, February 21st may be the starting day and the time period from February 21st to March 21 may be hidden. Similarly, in the case where no medical care data of the test A is found since June 1st, June 1st may be the starting day and the time period from June 1st to July 1st may be hidden. It should be noted that the one month at this time is 30 days.

Further, the length of a hidden time period may not necessarily be the same as the hidden time period determining length. Specifically, if the determination unit 13 determines that there is a time period which contains no medical care data and is equal to or longer than the hidden time period determining length, and no medical care data is found for a time period before or after the hidden time period determining length, the time period before or after the hidden time period determining length may also be hidden. For example, in the case where a time period which contains no medical care data of the test A and is equal to or longer than one month is March, and no medical care data of the test A is found in time periods before and after March, as in the graph shown in FIG. 4, the time periods before and after March may also be hidden. Specifically, in the case of the graph shown in FIG. 4, no medical care data of the test A is found from February 21st to April 15th, and therefore the time period from February 21st to April 15th, which includes time periods before and after March, may be hidden, as in the graph shown in FIG. 6. It should be noted that, while time periods before and after the hidden time period determining length are hidden in this example, only a time period before or after the hidden time period determining length may be hidden. For example, the time period from February 21st to March 31st may be hidden, or the time period from March 1st to April 15th may be hidden.

Figure 6:
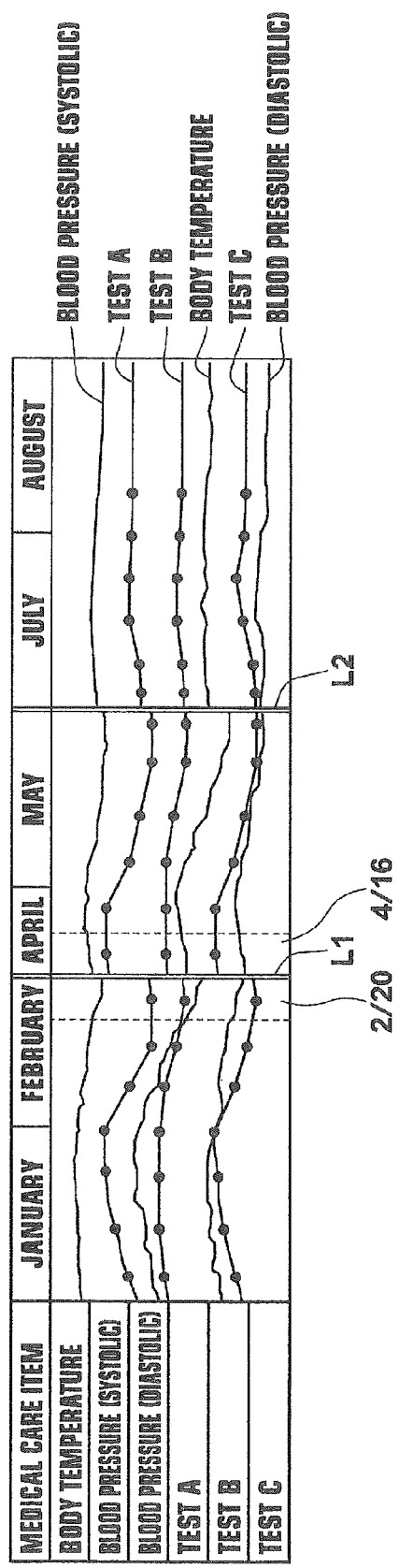
FIG. 6 shows an example where some parts of the time period of the graph shown in FIG. 4 are hidden.

Further, in the case where a part of the time period is hidden, as described above, it is desirable to display each line connecting the medical care data immediately before the hidden time period and the medical care data in the hidden time period or each line connecting the medical care data immediately after the hidden time period and the medical care data in the hidden time period, as shown in FIG. 5 or 6. By displaying such lines in the graph, the user can recognize the discontinuity in the graph and can recognize that there is a hidden time period. It should be noted that, in this case, the boundary lines L1 and L2 may be omitted since the user can recognize the discontinuities in the graph to recognize the positions of the hidden time periods.

Further, as described above, the hidden time period determining length may be arbitrarily selected and set by the user, or may be set in advance in the hidden time period determining length setting unit 14. In the latter case, the user specifies a medical care item for which the determination based on the hidden time period determining length is performed without selecting the hidden time period determining length.

Although the user specifies a medical care item for which the determination based on the hidden time period determining length is performed in the above-described embodiment, the determination based on the hidden time period determining length may be performed on all the medical care items as default setting, without receiving a user's specification.

The graph display mode where the display control unit 15 displays a graph of the medical care data has been described. Next, a numerical display mode where the medical care data are displayed in the form of numerical texts is described. FIG. 7 shows one example of a medical care information display screen in the numerical display mode.

In the medical care data display column R4 in the numerical display mode, numerical texts of the medical care data are displayed, as shown in FIG. 7. In the medical care data display column R4, each column extending in the vertical direction corresponds to each date, and each row extending in the horizontal direction corresponds to each medical care item. Further, in the drug administration period display column R3 in the numerical display mode, doses of administered or infused drugs are displayed in the form of numerical texts. In the drug administration period display column R3, each column extending in the vertical direction represents the date, and each row extending in the horizontal direction represents the type of an administered or infused drug.

Also in the numerical display mode, the drug list and the check boxes are displayed in the administered drug list display column R6. Then, when the check box of a given drug is checked, the row showing numerical values of administrated doses of the drug is highlighted by being displayed in a different color from the color of other parts, for example. In the medical care item list display column R7, the list of medical care items, and the highlighting check boxes CB1 and the hidden time period-determination check boxes CB2 are displayed, similarly to the graph display mode. When the highlighting check box CB1 is checked, a row showing numerical values of the medical care data of the checked medical care item is highlighted by being displayed in a different color from the color of other parts, for example.

Other features of the medical care information display screen in the numerical display mode, other than displaying the medical care data, the doses of administered drugs, etc., in the form of numerical texts (character strings) in place of a graph, are the same as those of the medical care information display screen in the graph display mode. Also in the numerical display mode, the hidden time period determining length is set, whether or not there is a time period which contains no, medical care data and is equal to or longer than the hidden time period determining length is determined, and if there is such a time period, the time period which contains no medical care data can be hidden.

Now, a specific display example is described. FIG. 8 shows an example where numerical values of medical care data of body temperature, blood pressure (systolic), blood pressure (diastolic), and tests A to C for an initial displayed time period, which is set to be January 5th to January 17th, obtained by the display control unit 15 are displayed in the form of texts. As described above, each column of the table shown in FIG. 8 corresponds to each date, and each row corresponds to each medical care item.

With respect to the display of the medical care data, as shown in FIG. 8, if the user wishes to observe, for example, the medical care data of the test A for a time period longer than the initial displayed time period at a time in an efficient manner, the user checks the hidden time period-determination check box CB2 for the test A in the medical care item list display column R7, and selects one of hidden time period determining lengths shown in the drop-down list DL. It is assumed here that a time period of one day is selected and set by the user as the hidden time period determining length.

The information specifying the test A and the information of the hidden time period determining length are outputted to the determination unit 13, and the determination unit 13 determines whether or not there is a time period which contains no medical care data of the test A and is equal to or longer than one day.

If there is a time period which contains no medical care data of the test A and is equal to or longer than one day, the result of determination is outputted to the display control unit 15, and the display control unit 15 hides the time period which contains no medical care data. Specifically, in the numerical display shown in FIG. 8, for example, the period from January 5th to January 7th, the period from January 9th to January 14th, and the period from January 16th to January 17th are the time periods which contain no medical care data of the test A and are equal to or longer than one day.

Then, the result of determination is outputted to the display control unit 15, and the display control unit 15 hides the time period from January 5th to January 7th, the time period from January 9th to January 14th, and the time period from January 16th to January 17th, as shown in FIG. 9. As the result of hiding the time period from January 5th to January 7th, the time period from January 9th to January 14th, and the time period from January 16th to January 17th, a blank is created along the horizontal direction in the medical care data display column R4. Then, the display control unit 15 obtains additional medical care data of all the items for a time period different from the initial displayed time period, and displays the medical care data of January 8th and January 15th where the medical care data of the test A is found, and additional medical care data of the same number of days as the number of the hidden days. Also at this time, time periods which contain no medical care data of the test A and are equal to or longer than one day are hidden. In this example, the medical care data of the test A of 11 days corresponding to the number of the hidden days are additionally displayed, and the user can observe the data of the test A for three months. Further, in a case where the tests A to C are tests that are performed according to one test order, medical care data of the tests A to C performed according to one test order can be observed at a time by selecting the test A.

The display with the time period determined based on the medical care data of the test A, as shown in FIG. 9, allows the user to efficiently perform diagnosis based on the medical care data of the test A.

Although a time period of one day is set as the hidden time period determining length, this is not intended to limit the invention. Similarly to the case of the graph display mode, one week or one month may be set as the hidden time period determining length.

Further, when a given time period is hidden, it is desirable to display a marker that allows the user to recognize that there is a hidden time period, similarly to the case of the graph display mode. For example, the boundary line of each hidden column may be shown in a different color from the color of other lines so that it is recognizable by the user, or an arrow or a marker, such as characters, indicating the position of the boundary line of each hidden column may be displayed. In the numerical display mode, where the presence of a hidden time period cannot be judged from discontinuity of lines of a graph, it is particularly important to clearly distinguish the boundary of each hidden time period.

In the numerical display mode, the hidden time period determining length may be arbitrarily selected and set by the user, or may be set in advance in the hidden time period determining length setting unit 14, similarly to the graph display mode.

In the numerical display mode, the determination based on the hidden time period determining length may be performed on all the medical care items as default setting, without receiving a user's specification of a medical care item for which the determination based on the hidden time period determining length is performed, similarly to the graph display mode.

Further, a medical care item with relatively low test frequency (which is a medical care item other than medical care items with relatively high test frequency, such as body temperature and blood) may be set in advance as a medical care item for which the determination based on the hidden time period determining length is performed. In this case, the hidden time period-determination check box CB2 may be provided only for a medical care item with low test frequency, or no hidden time period-determination check box CB2 may be provided for all the medical care items. This allows checking medical care items with high test frequency and medical care items with low test frequency in a simple and efficient manner.

Although the unit of the horizontal axis of the medical care data is a day in the above-described embodiment, this is not intended to limit the invention. The unit of the horizontal axis may be an hour or a month depending on the medical care data. The hidden time period determining length is set as appropriate depending on the unit of the time period represented by the horizontal axis of the medical care data.

Although the display is switched between the numerical display mode and the graph display mode in the above-described embodiment, this is not intended to limit the invention. Both the numerical texts and the graph may be displayed at a time on the same screen. Also in this case, the hidden time period determination can be performed in the same manner as in the above-described embodiment.

Although the examples where at least a time period equal to the hidden time period determining length is hidden are described in the above-described embodiment, an actual hidden time period, which is a time period shorter than the hidden time period determining length, may be set as a set value separately from the hidden time period determining length, and a time period corresponding to the actual hidden time period may be hidden. For example, in a case where test data is found in the time period from June 1st to June 30th and the time period from August 1st to August 31st, and a time period of 31 days is set as the hidden time period determining length, it is determined to hide the time period corresponding to July. However, if a time period of 20 days is set as the actual hidden time period, the time period from July 6th to July 25th is hidden. As a result, a blank time period of 11 days is displayed between the test data of June 30th and the test data of August 1st, and this allows clear visual recognition of the hidden time period.

What is claimed is:

1. A medical care data display control device for displaying medical care data of a plurality of items obtained in chronological order, the device comprising:
　a hidden time period determining length specification receiving unit configured to receive a specification of a hidden time period determining length for determining whether or not to hide a portion of the display period of the medical care data;
　a hidden time period determining unit, in which the hidden time period determining length is set;
　a determination unit that determines whether or not there is a time period which contains no medical care data and is equal to or longer than the hidden time period determining length; and
　a display control unit that hides, if it is determined by the determination unit that there is a time period which contains no medical care data and is equal to or longer than the hidden time period determining length, all or a part of the time period which contains no medical care data, the display control unit adding medical care data for a period different from a display period prior to being hidden and displaying the added medical care data in the case that a time period is determined to be hidden.

2. The medical care data display control device as claimed in claim 1, wherein the hidden time period comprises a time period including at least the hidden time period determining length.

3. The medical care data display control device as claimed in claim 1, further comprising an item specification receiving unit that receives a specification of an item for which the determination based on the hidden time period determining length is performed among the plurality of items,
　wherein the determination unit determines whether or not there is a time period which contains no medical care data of the specified item and is equal to or longer than the hidden time period determining length, and
　the display control unit hides, if it is determined that there is a time period which contains no medical care data of the specified item and is equal to or longer than the hidden time period determining length, all or a part of the time period which contains no medical care data of the specified item.

4. The medical care data display control device as claimed in claim 1, wherein the hidden time period determining length is set in advance.

5. The medical care data display control device as claimed in claim 1, wherein, if it is determined that there is a time period which contains no medical care data and is equal to or longer than the hidden time period determining length, and if there is a time period which contains no medical care data before or after the hidden time period determining length, the display control unit also hides the time period before or after the hidden time period determining length.

6. The medical care data display control device as claimed in claim 1, wherein the display control unit displays a marker that allows recognition of the hidden time period.

7. The medical care data display control device as claimed in claim 1, wherein the display control unit displays the medical care data in the form of a graph.

8. The medical care data display control device as claimed in claim 7, wherein the display control unit displays the graph with lines connecting the medical care data immediately before the hidden time period and the medical care data in the hidden time period or lines connecting the medical care data immediately after the hidden time period and the medical care data in the hidden time period.

9. The medical care data display control device as claimed in claim 1, wherein the display control unit displays the medical care data in the form of numerical texts.

10. The medical care data display control device as claimed in claim 1, wherein, when the time period which contains no medical care data is hidden, the display control unit additionally displays the medical care data for a time period that is different from the displayed time period before the time period which contains no medical care data is hidden.

11. The medical care data display control device as claimed in claim 1, wherein the display control unit hides an entirety of a time period which contains no medical data if results of determination by the determination unit are affirmative.

12. The medical care data display control device as claimed in claim 1, wherein the display control unit hides the medial data such that medical care data for an item for which a testing frequency is less than a predetermined value is automatically hidden for time periods during which the medical care data for the item are not present.

13. A medical care data display control method for displaying medical care data of a plurality of items obtained in chronological order, the method comprising:
　receiving a specification of a hidden time period determining length for determining whether or not to hide a portion of the display period of the medical care data;
　setting the hidden time period determining length;
　determining whether or not there is a time period which contains no medical care data and is equal to or longer than the hidden time period determining length; and
　if it is determined that there is a time period which contains no medical care data and is equal to or longer than the hidden time period determining length, all or a part of the time period which contains no medical care data is hidden,
　wherein medical care data is added for a period different from a display period prior to being hidden and the added medical care data is displayed in the case that a time period is determined to be hidden.

14. A non-transitory computer readable medium containing a medical care data display control program for causing a computer to function as a medical care data display control device for displaying medical care data of a plurality of items obtained in chronological order, the program causing the computer to function as:
　a hidden time period determining length specification receiving unit configured to receive a specification of a hidden time period determining length for determining whether or not to hide a portion of the display period of the medical care data;
　a hidden time period determining unit, in which the hidden time period determining length is set;
　a determination unit that determines whether or not there is a time period which contains no medical care data and is equal to or longer than the hidden time period determining length; and a display control unit that hides, if it is determined by the determination unit that there is a time period which contains no medical care data and is equal to or longer than the hidden time period determining length, all or a part of the time period which contains no medical care data, the display control unit adding medical care data for a period different from a display period prior to being hidden and displaying the added medical care data in the case that a time period is determined to be hidden.

* * * * *